United States Patent
Abbineni et al.

(10) Patent No.: US 7,365,216 B2
(45) Date of Patent: Apr. 29, 2008

(54) PROCESS FOR THE PRODUCTION OF CITALOPRAM

(75) Inventors: Jyothi Basu Abbineni, Hyderabad (IN); Hari Babu Bodepudi, Hyderabad (IN); Satyanarayana Chava, Hyderabad (IN); Venkata Ramana Rao Chunchu, Hyderabad (IN)

(73) Assignee: Matrix Laboratories Limited, Bollaram (IN)

( * ) Notice: Subject to any disclaimer, the term of this patent is extended or adjusted under 35 U.S.C. 154(b) by 672 days.

(21) Appl. No.: 10/475,907

(22) PCT Filed: Apr. 18, 2002

(86) PCT No.: PCT/IB02/03823

§ 371 (c)(1),
(2), (4) Date: Apr. 5, 2004

(87) PCT Pub. No.: WO03/072565

PCT Pub. Date: Sep. 4, 2003

(65) Prior Publication Data

US 2004/0259939 A1    Dec. 23, 2004

(51) Int. Cl.
*C07D 307/00* (2006.01)
(52) U.S. Cl. ..................................... 549/467
(58) Field of Classification Search ................. 549/467
See application file for complete search history.

(56) References Cited

U.S. PATENT DOCUMENTS

| 4,136,193 A | 1/1979 | Bogeso et al. .............. 424/285 |
| 2003/0144534 A1 | 7/2003 | Coppi et al. ................ 549/467 |

FOREIGN PATENT DOCUMENTS

| EP | 0 171 943 | 2/1986 |
| GB | 2356199 | 5/2001 |
| GB | 2357762 | 7/2001 |
| GB | 2 375 763 A | * 11/2002 |

* cited by examiner

*Primary Examiner*—Amelia A. Owens
(74) *Attorney, Agent, or Firm*—Vidas Arrett & Steinkraus

(57) ABSTRACT

The invention relates to a process for the manufacture of salts of citalopram in high purity. By the careful selection of solvents and the careful manipulation of the pH value, citalopram salts may be isolated in the absence of 5-chlorocitalopram, 5-bromocitalo-pram, desmethyl-citalopram and 5-carobxyamide citalopram.

4 Claims, No Drawings

PROCESS FOR THE PRODUCTION OF CITALOPRAM

This invention relates to citalopram, in particular salts of citalopram and a process for the manufacture of said salts in very high purity.

Citalopram is a well-known anti-depressant drug which has been on the market for a number of years. It has the structure shown below.

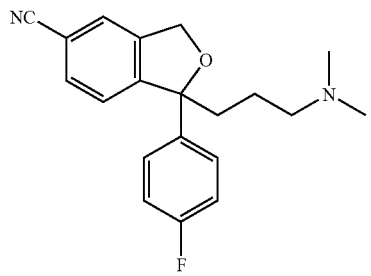

Citalopram is a selective, centrally acting serotonin (5-hydroxytryptamine:5-HT) re-uptake inhibitor and accordingly possesses anti-depressant activity. The anti-depressant activity of the compound has been reported in a number of publications and citalopram has further been disclosed as showing potential in the treatment of dementia and cerebrovascular disorders.

Citalopram was first disclosed in U.S. Pat. No. 4,136,193 which describes a number of processes for its preparation. Once manufactured, the citalopram base is generally converted to a salt using conventional procedures although it can be used as a free base. Hydrobromide salts are especially preferred since they are orally available.

Since the publication of the above mentioned U.S. Patent, a number of further processes for the preparation of citalopram have been devised and in many of these, as well as in the above U.S. Patent, the last step of the process involves the conversion of a group different from the cyano in the 5 position of the phthalane ring into the 5-cyano group. Preferably the conversion takes place from a bromine analogue.

As is well-known however, impurities are inevitably formed during the cyanation reaction and these impurities are difficult to separate from the desired end product. Impurities also remain from early synthesis stages and accordingly, extensive purification procedures are required.

Where the final stage of citalopram manufacture involves cyanation of 5-bromine analogue to the corresponding nitrile, the main impurities encountered are:

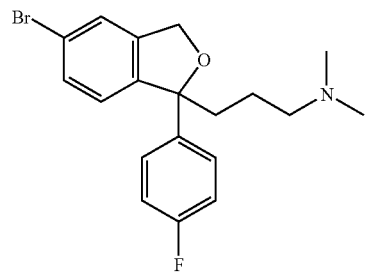

-continued

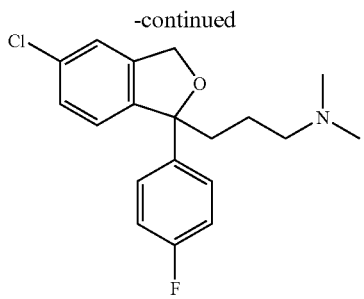

5-Br/Cl-citalopram

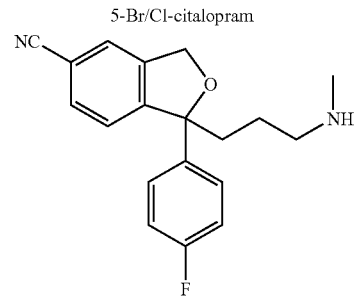

desmethyl citalopram

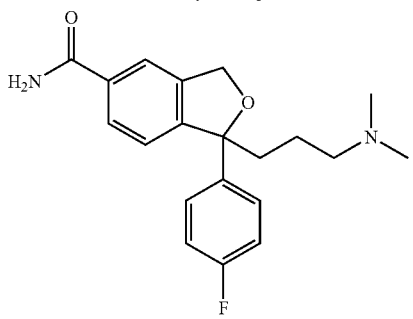

5-carboximade citalopram

Various purification procedures are already known in the art for purifying a crude citalopram mixture produced after such a cyanation reaction. For example, GB 2356199 teaches that the impurities may be removed using a conventional film distillation technique. The crude base is simply distilled using, for example, a thin film distillation apparatus yielding a purer citalopram material. The base product may then be formed into the salt. GB 2357762 describes an alternative procedure in which the crude free base is simply crystallised prior to conversion to the salt.

There still remains the need however, to devise efficient and more economic purifycation procedures especially for use on industrial scale where, for example, the use of film distillation apparatus may be prohibitively expensive.

The present inventors have now found an alternative and rapid way of isolating purer citalopram salts substantially in the absence of the above-mentioned impurities without using potentially time consuming crystallisation techniques or expensive film distillation apparatus. Rather, the present inventors have found that by the careful selection of solvents and the careful manipulation of pH, citalopram salts may be isolated in very high purity in the absence of the major impurities 5-chlorocitalopram, 5-bromocitalopram, desmethyl-citalopram and 5-carboxyamide citalopram.

Thus, viewed from one aspect the invention provides a process for the preparation of a salt of citalopram comprising:
(A) dissolving citalopram in a solvent selected from acetone, alcohol, or toluene or mixtures thereof and adding oxalic acid;
(B) separating the precipitated citalopram oxalate, e.g. by filtration;
(C) suspending said citalopram oxalate in water and adding a base in an amount sufficient to liberate citalopram, e.g. to a pH 9 to 10;
(D) extracting the liberated citalopram with an organic solvent, isolating the organic phase and evaporating said solvent;
optionally repeating steps (A) to (D),
repeating steps (A) and (B) and subsequently;
(E) suspending said citalopram oxalate in water and adding base to a pH 6 to 7;
(F) adding a solvent selected from toluene, cyclohexane, n-hexane, n-heptane, isopropyl ether or xylene or mixtures thereof and isolating the aqueous phase;
(G) adding base to said aqueous phase in an amount sufficient to liberate citalopram and extracting the liberated citalopram with an organic solvent, isolating the organic phase and evaporating said solvent;
(H) dissolving said citalopram in an alcohol solvent, adding an acid and separating the precipitated citalopram salt.

Viewed from another aspect the invention comprises a process for the separation of desmethyl citalopram from a crude mixture thereof with citalopram base comprising:
(A) dissolving citalopram in a solvent selected from acetone, alcohol, or toluene or mixtures thereof and adding oxalic acid;
(B) separating the precipitated citalopram oxalate;
(C) suspending said citalopram oxalate in water and adding a base in an amount sufficient to liberate citalopram, e.g. to a pH 9 to 10;
(D) extracting the liberated citalopram with an organic solvent, isolating the organic phase and evaporating said solvent;
optionally repeating steps (A) to (D).

Viewed from a still further aspect the invention provides a process for the separation of 5-chlorocitalopram and 5-bromocitalopram from a crude mixture of citalopram oxalate comprising:
(E) suspending citalopram oxalate in water and adding base to a pH 6 to 7;
(F) adding a solvent selected from toluene, cyclohexane, n-hexane, n-heptane, isopropyl ether or xylene or mixtures thereof and isolating the aqueous phase.

Viewed from another aspect the invention provides a process for the separation of 5-carboxyamide from a crude mixture of citalopram comprising:
(H) dissolving citalopram in an alcohol solvent, adding an acid and separating the precipitated salt, e.g. by filtration.

Viewed from a still yet further aspect the invention provides citalopram or salts thereof obtained by the processes of the invention as well as their use in medicine and pharmaceutical salts comprising the same.

As used herein "citalopram" refers to the free base thereof.

In part (A) of the process of the invention, the crude citalopram base should preferably be dissolved in acetone. Without wishing to be limited by theory, it is believed that desmethyl citalopram is removed in the solvent washings in step (B) when the citalopram oxalate salt is isolated. It has been found that the most efficient elimination of desmethyl citalopram occurs when the solvent employed is acetone.

Isolation of the precipitated citalopram oxalate in step (B) may be achieved by, for example, filtration or centrifugation or by any other conventional technique for separating a solid from a liquid. The citalopram oxalate is precipitated (it being insoluble in the organic solvent employed) and isolation should not be effected by evaporating off the organic phase since the desmethyl citalopram would, of course, not be removed in such a procedure.

The base used to liberate citalopram from its oxalate in step (C) may be any conventional base which is compatible with citalopram. Suitable bases include NaOH, KOH and various organic bases however, it is preferred if ammonia is used as the base. The pH of the solution in step (C) needs to be increased to a value sufficient to ensure citalopram base is liberated and the required pH will be readily determined by the skilled chemist. It is preferred however if the pH is adjusted to between 8.5 to 10, especially, 9.0 to 9.5, most preferably 9.0 to 9.2. The pH can of course be monitored using standard indicators or other pH measuring apparatus.

The liberated citalopram free base may be extracted from the aqueous solution by using a standard organic solvent (Step D). Most suitable in this regard is toluene although other hydrocarbon solvents such as xylene, hexane, heptane etc. could be employed equally successfully. The organic phase formed should be separated by a simple layer separation procedure and the solvent may then be evaporated off by simple distillation or under reduced pressure. Conveniently however, the solvent is removed under atmospheric pressure conditions so as to maintain the liberated citalopram as an oil. By using atmospheric pressure evaporation, it is likely that some traces of solvent will remain (perhaps up to 10%) hence maintaining the liberated citalopram in an oil form.

In order to remove any remaining traces of desmethyl citalopram it may be necessary to repeat the oxalate formation and subsequent base liberation steps (A to D).

Without wishing to be limited by theory, it is believed that the further main impurities, bromo/chloro citalopram can be removed by careful manipulation of pH and then by washing in particular solvents.

In order to remove these impurities according to the invention, it is necessary to add citalopram oxalate to water and adjust the pH of the solution to 6 to 7, preferably 6.2 to 7 (Step E). Again the base may be any base suitable for this task, e.g. as described above in relation to step (C), however, ammonia is again preferred.

The inventors have surprisingly found that at this pH citalopram oxalate remains substantially in its salt form but the salts of the chloro and bromo intermediates tend to convert back to their corresponding bases. On organic washing therefore (Step F), it has surprisingly proved possible to remove the impurities in the organic washings whilst maintaining the desired product in the aqueous phase. The organic washing solvent is conveniently toluene, cyclohexane, n-hexane, n-heptane, isopropyl ether or xylene or mixtures thereof. In a preferred embodiment the solvent is toluene, cyclohexane or a mixture thereof.

After the impurities have been removed in the organic phase, the aqueous layer can then be fully basified and the citalopram free base extracted into an organic solvent for subsequent conversion to the desired citalopram salt (Step G). Again, the solvent used to extract the liberated citalopram can be any solvent suitable for the task, e.g. those described above with respect to step (D).

Most suitable in this regard is again toluene although other hydrocarbon solvents such as xylene, hexane, heptane etc could be employed equally successfully. The solvent may then be evaporated off by simple distillation or under reduced pressure. Conveniently however, the solvent is removed under atmospheric pressure conditions so as to maintain the liberated citalopram as an oil. By using atmospheric pressure evaporation, it is likely that some traces of solvent will remain (perhaps up to 10%) hence maintaining the liberated citalopram in an oil form.

It is during the final stage, i.e. conversion to the desired salt, that the inventors believe that the 5-carboxyamide citalopram impurity may be removed.

This is achieved by dissolving the citalopram in an alcohol solvent, especially isopropyl alcohol or methanol. The aqueous salt forming agent, i.e. acid, is then added to form the citalopram salt (Step H). The citalopram salt crystals may be isolated conventionally by filtration or centrifugation but the 5-carboxyamide citalopram impurity remains in the organic phase and is hence easily and surprisingly removed with the organic phase.

The salt to be manufactured is preferably the hydrobromide, hydrochloride or oxalate salt.

The purification technique of the present invention is particularly suitable for preparing citalopram hydrobromide where the initial citalopram mixture has been prepared via a cyanation of 5-bromocitalopram. However, the process is equally suitable for the purification of the crude citalopram made by any other process. Other such processes are described in, for example, EP-A-171943.

The cyanation of bromocitalopram is easily carried out using, for example, sodium cyanide or preferably copper cyanide. Bromocitalopram itself can be manufactured in a number of ways, for example, as described in U.S. Pat. No. 4,136,193.

Depending on the nature of the impurities present it may be possible to omit some of the purification stages of the process of the invention. Thus, if no desmethyl citalopram is present in a crude citalopram mixture, it may be possible to omit stages (A) to (D) and simply remove the other impurities following the teaching of steps (E) to (H). This forms a further aspect of the invention. Similarly, if a 5-carboxyamide citalopram impurity is not present then conversion to the desired salt may be effected without following the explicit teachings of step (H). Hence the present invention also provides a process as described in steps (A) to (G) and steps (A) to (D) followed by step (H).

Citalopram salts made by the process of the invention may be formulated into pharmaceutical compositions as is well known in the art. Such compositions may take the form of tablets which may be prepared by mixing the active ingredient with ordinary adjuvants and/or diluents and subsequently compressing the mixture in a conventional tableting machine. Examples of adjuvants or diluents comprise: corn starch, potato starch, talcum, magnesium stearate, gelatin, lactose, gums and is the like. Any other adjuvant or additive colourings, aroma, preservatives, taste masking agents etc. may be used provided that they are compatible with the active ingredient.

The active ingredient may also be formulated as a solution for injection which may be prepared by solving the active ingredient and possible additives in a part of the solvent for injection, preferably sterile water, adjusting the solution to the desired volume, sterilisation of the solution and filling in suitable ampoules or vials. Again, any suitable additive conventionally used in the art may be added such as tonicity agents, preservatives, antioxidants, etc.

The amount of citalopram administered to a patient is dependent on the nature of the patient and will be readily determined by the skilled physician. Tablets may however comprise, for example, 20 mg or 40 mg doses.

Citalopram may be administered along with any other pharmaceutical with which it is compatible and additional active ingredients can of course be formulated into compositions with citalopram as is well known in the art.

The invention will now be further described with reference to the following non-limiting examples.

EXAMPLE 1

1-(3-Dimethylaminopropyl)-1-(4'-fluorophenyl)-1,3 dihydrobenzofuran-5-carbonitrile oxalate (Citalopram Oxalate)

Citalopram was prepared substantially as described in Example 2 of U.S. Pat. No. 4,136,193 although toluene was used instead of benzene. 100 g of citalopram (0.30 mol) with a desmethyl citalopram content of up to 5.0% was added to acetone (300 ml) and the resulting solution stirred for 15 min. at 40° C. To the above clear solution was added oxalic acid (40 g, 0.31 mol), dissolved in acetone (300 ml) and the resulting mixture heated to 50-55° C. The mixture was cooled and the white crystals of the title compound were filtered off at room temperature and dried at 60° C. for 6 hrs at atmospheric pressure.

Citalopram oxalate prepared as in Example 1 (105 g, 0.25 mol) was suspended in water (525 ml) and the pH was adjusted to 9.0-9.2 by the addition of ammonia. The mixture was stirred for 30 minutes and extracted with toluene twice (250 ml). The organic phases were separated and washed with water (100 ml). Toluene layer was concentrated under vacuum. Acetone (300 ml) is added to the residue and the mixture stirred for 15 min. at 40° C. To the above clear solution was added oxalic acid (33 g, 0.26 mol), dissolved in Acetone (300 ml) and the mixture was heated to 50-55° C. The white crystals of the title compound were filtered off at room temperature and dried at 60° C. for 6 hrs at atmospheric pressure.

Yield: 90 g (85%). Desmethyl citalopram content less than 0.1%.

EXAMPLE 2

1-(3-Dimethylaminopropyl)-1-(4'-fluorophenyl)-1,3 dihydrobenzofuran-5-carbonitrile hydrobromide (Citalopramhydrobromide)

1-(3-Dimethylaminopropyl)-1-(4'-fluorophenyl)-1,3-dihydrobenzofuran-5-carbonitrile oxalate (90 g, 0.21 mol) prepared as per example 1 was suspended in water (500 ml) and aqueous ammonia (20-25%) was added to adjust the pH of the solution to 6.2-7.0 (approximately 20 ml). The solution is stirred for 15 min. The above solution was washed with toluene (6×50 ml) and the organic phases are separated. To the remaining aqueous phase was added ammonia (20-25%) to bring the pH to 9.0-9.2. The mixture was stirred for 15 min, and extracted with toluene (2×250 ml). The organic phases were washed with NaCl solution (100 ml, 10%) and the toluene removed in vacuum to leave an oily residue. To the residue was added 350 ml isopropylalcohol and the clear solution filtered through Celite®. To the resulting clear solution is added 35 g of 48% aq. hydrobromic acid and the mixture is stirred for 1 hr at 50° C. After cooling to 20° C., the crystals are filtered and dried.

Yield: 75 g (85%) Purity: 99.7%

The invention claimed is:

1. A process for the preparation of a salt of citalopram comprising: (A) dissolving citalopram in a solvent selected from acetone, alcohol, or toluene or mixtures thereof and adding oxalic acid; (B) separating the precipitated citalopram oxalate; (C) suspending said citalopram oxalate in water and adding a base in an amount sufficient to liberate citalopram; (D) extracting the liberated citalopram with an organic solvent, isolating the organic phase and evaporating said solvent; optionally repeating steps (A) to (D), repeating steps (A) and (B) and subsequently; (E) suspending said citalopram oxalate in water and adding base to a pH 6 to 7; (F) adding a solvent selected from toluene, cyclohexane, n-hexane, n-heptane, isopropyl ether or xylene or mixtures thereof and isolating the aqueous phase; (G) adding base to said aqueous phase in an amount sufficient to liberate citalopram and extracting the liberated citalopram with an organic solvent, isolating the organic phase and evaporating said solvent; (H) dissolving said citalopram in an alcohol solvent, adding an acid and separating the precipitated citalopram salt.

2. A process for the separation of desmethyl citalopram from a crude mixture thereof with citalopram base comprising: (A) dissolving citalopram in a solvent selected from acetone, alcohol, or toluene or mixtures thereof and adding oxalic acid; (B) separating the precipitated citalopram oxalate; (C) suspending said citalopram oxalate in water and adding a base in an amount sufficient to liberate citalopram; (D) extracting the liberated citalopram with an organic solvent, isolating the organic phase and evaporating said solvent; optionally repeating steps (A) to (D).

3. A process for the separation of 5-chlorocitalopram and 5-bromocitalopram from a crude mixture of citalopram oxalate comprising: (E) suspending citalopram oxalate in water and adding base to a pH 6 to 7; (F) adding a solvent selected from toluene, cyclohexane, n-hexane, n-heptane, isopropyl ether or xylene or mixtures thereof and isolating the aqueous phase.

4. A process for the separation of 5-carboxyamide from a crude mixture of citalopram comprising: (H) dissolving citalopram in an alcohol solvent, adding an acid and separating the precipitated salt.

* * * * *